(12) United States Patent
Witchey et al.

(10) Patent No.: US 12,094,574 B2
(45) Date of Patent: Sep. 17, 2024

(54) DIFFERENCE-BASED GENOMIC IDENTITY SCORES

(71) Applicant: Nantomics, LLC, Culver City, CA (US)

(72) Inventors: Nicholas J. Witchey, Culver City, CA (US); Patrick Soon-Shiong, Culver City, CA (US); Kayvan Niazi, Culver City, CA (US); John Zachary Sanborn, Culver City, CA (US)

(73) Assignee: NantOmics, LLC, Culver City, CA (US)

(*) Notice: Subject to any disclaimer, the term of this patent is extended or adjusted under 35 U.S.C. 154(b) by 19 days.

(21) Appl. No.: 16/972,520

(22) PCT Filed: Jun. 6, 2019

(86) PCT No.: PCT/US2019/035786
§ 371 (c)(1),
(2) Date: Dec. 4, 2020

(87) PCT Pub. No.: WO2019/236842
PCT Pub. Date: Dec. 12, 2019

(65) Prior Publication Data
US 2021/0313012 A1    Oct. 7, 2021

Related U.S. Application Data

(60) Provisional application No. 62/681,800, filed on Jun. 7, 2018.

(51) Int. Cl.
*G16B 30/10* (2019.01)
*G16B 20/20* (2019.01)
*G16B 40/30* (2019.01)

(52) U.S. Cl.
CPC ............. *G16B 30/10* (2019.02); *G16B 20/20* (2019.02); *G16B 40/30* (2019.02)

(58) Field of Classification Search
None
See application file for complete search history.

(56) References Cited

U.S. PATENT DOCUMENTS 7,917,302 B2  3/2011 Rognes
9,646,134 B2  5/2017 Sanborn et al.
(Continued)

FOREIGN PATENT DOCUMENTS

CN   103403182 A   11/2013
CN   105814573 A   7/2016
(Continued)

OTHER PUBLICATIONS

Roth, A.; Ding, J.; Morin, R.; Crisan, A.; Ha, G.; Giuliany, R.; Bashashati, A.; Hirst, M.; Turashvili, G.; Oloumi, A.; Marra, M. A.; Aparicio, S.; Shah, S. P. JointSNVMix: A Probabilistic Model for Accurate Detection of Somatic Mutations in Normal/Tumour Paired next-Generation Sequencing Data. Bioinformatics 2012, 28 (7), 907-913.*

(Continued)

*Primary Examiner* — Soren Harward
(74) *Attorney, Agent, or Firm* — Martin Fessenmaier; Umberg Zipser LLP

(57) ABSTRACT

Methods for analyzing omics data and using the omics data to determine genetic distances and/or difference scores among a plurality of biological uncles to so further determine the homogeneity of a group having a plurality of biological samples and/or exclude as individual biological sample from a group of biological samples a an outlier we presented. In preferred methods, a plurality of local differential string sea among do plurality of sequence strings is (Continued)

generated wing a plurality of local alignments. The local different suing is as indicative of genetic difference between one sequence string and one of do rests of do sequence strings among the plurality of sequence strings. From the plurality of local differential string sets, a plurality of difference scores among do plurality of sequence strings can be determined.

18 Claims, 8 Drawing Sheets

Specification includes a Sequence Listing.

(56) References Cited

U.S. PATENT DOCUMENTS

| | | | |
|---|---|---|---|
| 9,652,587 B2 | 5/2017 | Sanborn et al. | |
| 9,721,062 B2 | 8/2017 | Sanborn et al. | |
| 9,824,181 B2 | 11/2017 | Sanborn et al. | |
| 2004/0235158 A1* | 11/2004 | Bartlett | A61P 25/28 435/366 |
| 2007/0067108 A1 | 3/2007 | Buhler et al. | |
| 2009/0327170 A1* | 12/2009 | Donati | A61K 39/00 424/139.1 |
| 2012/0059670 A1 | 3/2012 | Sanborn et al. | |
| 2012/0066001 A1 | 3/2012 | Sanborn et al. | |
| 2017/0199959 A1 | 7/2017 | Locke | |
| 2018/0044730 A1 | 2/2018 | Pickrell et al. | |

FOREIGN PATENT DOCUMENTS

| | | |
|---|---|---|
| KR | 10-2004-0051748 A | 6/2004 |
| TW | 201639879 A | 11/2016 |
| TW | 201816645 A | 5/2018 |
| TW | 202013385 A | 4/2020 |
| WO | 2019/236842 A1 | 12/2019 |

OTHER PUBLICATIONS

Larson, D. E.; Harris, C. C.; Chen, K.; Koboldt, D. C.; Abbott, T. E.; Dooling, D. J.; Ley, T. J.; Mardis, E. R.; Wilson, R. K.; Ding, L. SomaticSniper: Identification of Somatic Point Mutations in Whole Genome Sequencing Data. Bioinformatics 2012, 28 (3), 311-317.*

Li et al., "The Sequence Alignment/Map format and SAMtools", Bioinformatics, 2009, vol. 25, No. 16, pp. 2078-2079 (Cited from Specification).

"Sequence Alignment/Map Format Specification, The SAM/BAM Format Specification Working Group", 2020, pp. 1-23 (Cited from Specification).

Li et al., "Mapping short DNA sequencing reads and calling variants using mapping quality scores", Genome Research, 2008, vol. 18, pp. 1851-1858 (Cited from Specification).

Goya et al., "SNVMix: predicting single nucleotide variants from next-generation sequencing of tumors", Bioinformatics, 2010, vol. 26, No. 6, pp. 730-736 (Cited from Specification).

Cibulskis et al., "Sensitive detection of somatic point mutations in impure and heterogeneous cancer samples", Nature Biotechnology, 2013, vol. 31, No. 3, pp. 213-219 (Cited from Specification).

Saunders et al., "Strelka: accurate somatic small-variant calling from sequenced tumor-normal sample pairs", Bioinformatics, 2012, vol. 28, No. 14, pp. 1811-1817 (Cited from Specification).

International Search Report and Written Opinion received for PCT Application Serial No. PCT/US2019/035786 dated Oct. 18, 2019, 9 pages.

Simmons et al., "The effects of increasing genetic distance on alignment of, and tree construction from, rDNA internal transcribed spacer sequences", Molecular Phylogenetics and Evolution, 2003, vol. 26, pp. 444-451.

Office Action received for Taiwanese Patent Application Serial No. 108119097 dated Aug. 24, 2020, 19 pages (Including English translation).

International Preliminary Report on Patentability Chapter I received for PCT Application Serial No. PCT/US2019/035786 dated Dec. 17, 2020, 8 pages.

Office Action received for Taiwanese Patent Application Serial No. 108119097 dated Dec. 10, 2020, 4 pages (Including English translation).

* cited by examiner

```
@HD  VN:1.5  SO:coordinate
@SQ  SN:ref  LN:45
r001   99 ref   7 30 8M2I4M1D3M   = 37  39 TTAGATAAAGGATACTG  *   SEQ ID NO: 1
r002    0 ref   9 30 3S6M1P1I4M   *  0   0 AAAAGATAAGGATA      *   SEQ ID NO: 2
r003    0 ref   9 30 5S6M         *  0   0 GCCTAAGCTAA         *   SA:Z:ref,29,-,6H5M,17,0;
r004    0 ref  16 30 6M14N5M      *  0   0 ATAGCTTCAGC         *   SEQ ID NO: 4
r003 2064 ref  29 17 6H5M         *  0   0 TAGGC               *   SA:Z:ref,9,+,5S6M,30,1;
r001  147 ref  37 30 9M           =  7 -39 CAGCGGCAT           *   NM:i:1
```

SEQ ID NO: 3

Figure 3

|    | 1      | 2      | 3      | 4      | 5      | 6      | 7      | 8      | 9      | 10     |
|----|--------|--------|--------|--------|--------|--------|--------|--------|--------|--------|
| 1  |        | -4.828 | -4.826 | -7.944 | -4.860 | -7.960 | -4.826 | -7.945 | -4.828 | -4.828 |
| 2  | -4.828 |        | -4.842 | -4.828 | -4.847 | -4.828 | -4.841 | -4.827 | -7.942 | -7.923 |
| 3  | -4.826 | -4.842 |        | -4.827 | -4.848 | -4.827 | -7.952 | -4.826 | -4.842 | -4.840 |
| 4  | -7.944 | -4.828 | -4.827 |        | -4.860 | -7.937 | -4.827 | -7.957 | -4.828 | -4.828 |
| 5  | -4.860 | -4.847 | -4.848 | -4.860 |        | -4.860 | -4.849 | -4.859 | -4.847 | -4.846 |
| 6  | -7.960 | -4.828 | -4.827 | -7.937 | -4.860 |        | -4.827 | -7.968 | -4.828 | -4.828 |
| 7  | -4.826 | -4.841 | -7.952 | -4.827 | -4.849 | -4.827 |        | -4.827 | -4.842 | -4.841 |
| 8  | -7.945 | -4.827 | -4.826 | -7.957 | -4.859 | -7.968 | -4.827 |        | -4.828 | -4.827 |
| 9  | -4.828 | -7.942 | -4.842 | -4.828 | -4.847 | -4.828 | -4.842 | -4.828 |        | -7.931 |
| 10 | -4.828 | -7.923 | -4.840 | -4.828 | -4.846 | -4.828 | -4.841 | -4.827 | -7.931 |        |

Figure 7

|   | A | | | B | | | | C | | D |
|---|---|---|---|---|---|---|---|---|---|---|
|   | 10 | 2 | 9 | 6 | 8 | 4 | 1 | 7 | 3 | 4 |
| 10 |  | -7.923 | -7.931 | -4.828 | -4.827 | -4.828 | -4.828 | -4.841 | -4.840 | -4.846 |
| 2 | -7.923 |  | -7.942 | -4.828 | -4.827 | -4.828 | -4.828 | -4.841 | -4.842 | -4.847 |
| 9 | -7.931 | -7.942 |  | -4.828 | -4.828 | -4.828 | -4.828 | -4.842 | -4.842 | -4.847 |
| 6 | -4.828 | -4.828 | -4.828 |  | -7.968 | -7.937 | -7.960 | -4.827 | -4.827 | -4.860 |
| 8 | -4.827 | -4.827 | -4.828 | -7.968 |  | -7.957 | -7.945 | -4.827 | -4.826 | -4.859 |
| 4 | -4.828 | -4.828 | -4.828 | -7.937 | -7.957 |  | -7944 | -4.827 | -4.827 | -4.860 |
| 1 | -4.828 | -4.828 | -4.828 | -7.960 | -7.945 | -7.944 |  | -4.826 | -4.826 | -4.860 |
| 7 | -4.841 | -4.841 | -4.842 | -4.827 | -4.827 | -4.827 | -4.826 |  | -7.952 | -4.849 |
| 3 | -4.840 | -4.842 | -4.842 | -4.827 | -4.826 | -4.827 | -4.826 | -7.952 |  | -4.848 |
| 4 | -4.846 | -4.847 | -4.847 | -4.860 | 4.859 | -4.860 | -4.860 | -4.849 | -4.848 |  |

Figure 8

SEQUENCE LISTING

<160> NUMBER OF SEQ ID NOS: 24

<210> SEQ ID NO 1
<211> LENGTH: 16
<212> TYPE: DNA
<213> ORGANISM: Artificial Sequence
<220> FEATURE:
<223> OTHER INFORMATION: R001

<400> SEQUENCE: 1
ttagatmagg atactg                                                    16

<210> SEQ ID NO 2
<211> LENGTH: 14
<212> TYPE: DNA
<213> ORGANISM: Artificial Sequence
<220> FEATURE:
<223> OTHER INFORMATION: R002

<400> SEQUENCE: 2
aaaagataag gata                                                      14

<210> SEQ ID NO 3
<211> LENGTH: 11
<212> TYPE: DNA
<213> ORGANISM: Artificial Sequence -continued

<220> FEATURE:
<223> OTHER INFORMATION: R003

<400> SEQUENCE: 3
gcctaagcta a                                                              11

<210> SEQ ID NO 4
<211> LENGTH: 11
<212> TYPE: DNA
<213> ORGANISM: Artificial Sequence
<220> FEATURE:
<223> OTHER INFORMATION: R004

<400> SEQUENCE: 4
atagcttcag c                                                              11

<210> SEQ ID NO 5
<211> LENGTH: 36
<212> TYPE: DNA
<213> ORGANISM: Artificial Sequence
<220> FEATURE:
<223> OTHER INFORMATION: Pos 1

<400> SEQUENCE: 5
cactagtggc tcattgtaaa tgtgtggttt aactcg                                   36

<210> SEQ ID NO 6
<211> LENGTH: 35
<212> TYPE: DNA
<213> ORGANISM: Artificial Sequence
<220> FEATURE:
<223> OTHER INFORMATION: Pos 3

<400> SEQUENCE: 6
ctagtggctc attgtaaatg tgtggtttaa ctcgt                                    35

<210> SEQ ID NO 7
<211> LENGTH: 35
<212> TYPE: DNA
<213> ORGANISM: Artificial Sequence
<220> FEATURE:
<223> OTHER INFORMATION: Pos 5

<400> SEQUENCE: 7
agtggctcat tgtaaatgtg tggtttaact cgtcc                                    35

<210> SEQ ID NO 8
<211> LENGTH: 36
<212> TYPE: DNA
<213> ORGANISM: Artificial Sequence
<220> FEATURE:
<223> OTHER INFORMATION: Pos 6

<400> SEQUENCE: 8
gtggctcatt gtaattttt gttttaactc ttctct                                    36

<210> SEQ ID NO 9
<211> LENGTH: 35
<212> TYPE: DNA
<213> ORGANISM: Artificial Sequence
<220> FEATURE:
<223> OTHER INFORMATION: Pos 9

<400> SEQUENCE: 9
gctcattgta aatgtgtggt ttaactcgtc catgg                                    35

```
<210> SEQ ID NO 10
<211> LENGTH: 35
<212> TYPE: DNA
<213> ORGANISM: Artificial Sequence
<220> FEATURE:
<223> OTHER INFORMATION: Pos 13a

<400> SEQUENCE: 10
attgtaaatg tgtggtttaa ctcgtccctg gccca                        35

<210> SEQ ID NO 11
<211> LENGTH: 36
<212> TYPE: DNA
<213> ORGANISM: Artificial Sequence
<220> FEATURE:
<223> OTHER INFORMATION: Pos 13b

<400> SEQUENCE: 11
attgtaaatg tgtggtttaa ctcgtccatg gcccag                       36

<210> SEQ ID NO 12
<211> LENGTH: 33
<212> TYPE: DNA
<213> ORGANISM: Artificial Sequence
<220> FEATURE:
<223> OTHER INFORMATION: Synchronized read 1

<400> SEQUENCE: 12
gtgaatgtgt ggtttacctc gtccatggcc cag                          33

<210> SEQ ID NO 13
<211> LENGTH: 35
<212> TYPE: DNA
<213> ORGANISM: Artificial Sequence
<220> FEATURE:
<223> OTHER INFORMATION: Synchronized read 2

<400> SEQUENCE: 13
attgtgaatg tgtggtttac ctcgtccatg gccca                        35

<210> SEQ ID NO 14
<211> LENGTH: 33
<212> TYPE: DNA
<213> ORGANISM: Artificial Sequence
<220> FEATURE:
<223> OTHER INFORMATION: Synchronized read 3

<400> SEQUENCE: 14
tggctcattg tgaatgtgtg gtttacctcg tcc                          33

<210> SEQ ID NO 15
<211> LENGTH: 33
<212> TYPE: DNA
<213> ORGANISM: Artificial Sequence
<220> FEATURE:
<223> OTHER INFORMATION: Synchronized read 4

<400> SEQUENCE: 15
tggctcattg tgaatgtgtg gtttacctcg tag                          33

<210> SEQ ID NO 16
<211> LENGTH: 36
<212> TYPE: DNA
<213> ORGANISM: Artificial Sequence
<220> FEATURE:
<223> OTHER INFORMATION: Synchronized read 5
```

<400> SEQUENCE: 16
cactagtggc tcattgtgaa tgtgtggttt acctcg         36

<210> SEQ ID NO 17
<211> LENGTH: 36
<212> TYPE: DNA
<213> ORGANISM: Artificial Sequence
<220> FEATURE:
<223> OTHER INFORMATION: Synchronized read 6

<400> SEQUENCE: 17
cactagtggc tcattgtaaa tgtgtggttt aactcg         36

<210> SEQ ID NO 18
<211> LENGTH: 35
<212> TYPE: DNA
<213> ORGANISM: Artificial Sequence
<220> FEATURE:
<223> OTHER INFORMATION: Synchronized read 7

<400> SEQUENCE: 18
cactagtggc tcattggaat gtgtggttta tctcg          35

<210> SEQ ID NO 19
<211> LENGTH: 35
<212> TYPE: DNA
<213> ORGANISM: Artificial Sequence
<220> FEATURE:
<223> OTHER INFORMATION: Synchronized read 8

<400> SEQUENCE: 19
ctagtggctc attgtgaatg tgtggtttat ctcgt          35

<210> SEQ ID NO 20
<211> LENGTH: 34
<212> TYPE: DNA
<213> ORGANISM: Artificial Sequence
<220> FEATURE:
<223> OTHER INFORMATION: Synchronized read 9

<400> SEQUENCE: 20
agtggctcat tggaatgtgt ggtttatctc gtcc           34

<210> SEQ ID NO 21
<211> LENGTH: 36
<212> TYPE: DNA
<213> ORGANISM: Artificial Sequence
<220> FEATURE:
<223> OTHER INFORMATION: Synchronized read 10

<400> SEQUENCE: 21
gtggctcatt ctcatttttt gttttatctc ttctct         36

<210> SEQ ID NO 22
<211> LENGTH: 35
<212> TYPE: DNA
<213> ORGANISM: Artificial Sequence
<220> FEATURE:
<223> OTHER INFORMATION: Synchronized read 11

<400> SEQUENCE: 22
gctcattgtg aatgtgtggt ttatctcgtc catgg          35

<210> SEQ ID NO 23

```
<211> LENGTH: 35
<212> TYPE: DNA
<213> ORGANISM: Artificial Sequence
<220> FEATURE:
<223> OTHER INFORMATION: Synchronized read 12

<400> SEQUENCE: 23
attgtgaatg tgtggtttat ctcgtccctg gccca                              35

<210> SEQ ID NO 24
<211> LENGTH: 36
<212> TYPE: DNA
<213> ORGANISM: Artificial Sequence
<220> FEATURE:
<223> OTHER INFORMATION: Synchronized read 13

<400> SEQUENCE: 24
attgtcaatg tgtggtttat ctcgtccatg gcccag                             36
```

DIFFERENCE-BASED GENOMIC IDENTITY SCORES

This application claims priority to our U. S. provisional patent applications with the Ser. No. 62/681,800, filed Jun. 7, 2018 which is incorporated by reference in its entirety herein.

This application includes the contents of a nucleotide and amino acid sequence listing in computer readable form (CRF) as an ASCII text named 102690.0022US_ST25, which is 4,673 bytes in size, was created on 9/8/2022 and electronically submitted via EFS-Web.

FIELD OF THE INVENTION

The field of the invention is computational analysis of genomic data, particularly as it relates to determination of genomic distance within the same species or genetically modified organisms.

BACKGROUND OF THE INVENTION

With the increasing availability of whole genome data and the ever-increasing speed of whole genome sequencing, enormous quantities of data are now available that demand a meaningful analysis to so provide a clinician or scientist with information to enable more effective treatment or drug development.

Genetic homogeneity among biological samples including cells, tissues, or organisms can often be a critical factor to determine associations with genotypes and phenotypes of the biological samples, determine associations with genotypes to efficacies of drugs or treatment regimens, and also predict the likelihood of success of drugs or treatment regimens to the biological samples. Further, where the biological sample itself is a treatment regime (e.g. genetically modified calls, cancer vaccines, etc.), the genetic homogeneity of the biological sample can be attributed to more reliable and predictable treatment outcome in the patients.

Generally, genetic relatedness among two or more DNA samples can be determined by comparing DNA sequence information of the biological samples in an alignment of the DNA sequences and analyzing the difference among the aligned DNA sequences. In many cages, a biological sample is sequenced to an average read depth of 30× (same base position covered by at least 30 reads), a most likely genome is reconstructed using an aligner, and the so formed genome (or shorter sequence) is then aligned another genome or shorter sequence, typically by pairwise genetic distance. As will be readily apparent, such traditional method produces hundreds of gigabytes of sequence information data in compressed form, which renders analysis comparing a pair of these large datasets slow and difficult to manage. Further, as mere variations in raw DNA sequences of two biological samples may not necessarily reflect meaningful heterogeneity of such biological samples, current methods of measuring genetic distances often cannot provide accurate information how multiple biological samples are meaningfully related.

Thus, even though numerous methods of genomic analysis to measure genetic distances are known in the art, all or almost all of them suffer from several disadvantages. Most significantly, as heretofore known methods often weigh all differences in sequence alignments weighs equally, such methods can often underestimate or overestimate genetic differences among two samples. Additionally, the very large data files produced by genome sequencing are difficult to transport and process. Consequently, there is still a need to provide improved systems and methods for genomic analysis with improved data processing, and especially systems and methods that provide differentially weighed multi-factor approaches, to determine genetic distances among biological samples, and/or to determine homogeneity of a group of biological samples.

SUMMARY OF THE INVENTION

The present invention is directed to various systems and methods for genetic analysis, and especially genomic analysis to determine homogeneity of a group of biological samples by multiple, possibly incremental synchronous, sequence alignments. Thus, one aspect of the subject matter includes a method of determining genetic distances among a plurality of biological samples using sequencing data obtained from the biological samples. In this method, an access to a genetic database storing a first genetic sequence string representing a first biological sample and a second genetic sequence string representing a second biological sample is provided. The first and second sequence strings have a plurality of corresponding sub-strings. In addition, an access to a sequence analysis engine coupled with the genetic database is provided. Then, using the sequence analysis engine, a first local alignment by incrementally synchronizing the first and second sequence strings using a known position of at least one of plurality of corresponding substrings is produced. As a next step, sequence analysis engine uses the first local alignment to generate a first local differential string set between the first and second sequence strings. The local differential string set comprises at least one local different string. From the first local differential string set, a first difference score between the first and second genetic sequence strings can be determined. In a preferred embodiment, based on the first difference score, a first genetic distance between the first and second biological samples can be determined.

In some embodiments, the method can continue with analysis of producing a first local alignment by incrementally synchronizing the second and third local alignments by incrementally synchronizing the first and third sequence strings and second and third sequence strings, respectively, using a known position of at least one of plurality of corresponding sub-strings. Then, using the second and third local alignments, the sequence analysis engine can generate a second and third local differential string sets between the first and third, and between the second and third sequence strings within the local alignment, respectively. Preferably, the second and third local differential string sets comprise at least one local different string. From the second and third local differential string sets a second and third difference scores between the first and third and second and third genetic sequence strings, respectively, can be determined. Then, using the second and third difference scores, the second and third genetic distances between the first and third, and second and third biological samples, respectively.

Preferably, the local differential string comprises a nucleic acid sequence that is different between the first and second genetic sequence strings. In such embodiment, it is contemplated that the difference score can be associated with a length of the nucleic acid sequences and/or a number of nucleotides that are different between the first and second genetic sequence strings. In some embodiments, the local differential string set comprises a plurality of local differential strings between two sequence strings within the local alignment. In such embodiment, the difference score can be associated with a number of the local differential strings.

It is contemplated that the difference of nucleic acid sequence(s) in the local differential string may indicate at least one of a missense mutation, a nonsense mutation, an insertion, a deletion, a duplication, a frameshift mutation, a repeat expansion, an inversion, or a translocation. In such embodiment, the difference score can be determined based on is at least one of types of mutations and numbers of mutations in the nucleic acid sequence. Where the types of mutations determine the difference scone, different type of mutations may be associated with different scores.

It is also contemplated that the genetic distance can be determined based on the difference between the difference scores and a threshold value. Thus, in some embodiments, the homogeneity of a group of biological samples can be certified when the first, second and third genetic distances are under a threshold value. In other embodiments, a biological sample can be excluded from a group as an outlier if the genetic distance of the biological sample is at least 30%, or at least 50% farther than the genetic distances of other biological samples.

In another aspect of the inventive subject matter, the inventors contemplate a method of certifying homogeneity of a group having a plurality of biological samples, using sequencing data obtained from the biological samples. In this method, a plurality of local alignments are produced, using a sequence analysis engine, by incrementally synchronizing a plurality of sequence strings using a known position of at least one of plurality of corresponding substrings. The plurality of genetic sequence strings representing the plurality of biological samples, respectively, and the plurality of genetic sequence strings have a plurality of corresponding sub-strings. Than, using the plurality of local alignments, the sequence analysis engine to generate a plurality of local differential string sets among the plurality of sequence strings. Each of the plurality of local differential string sets comprises at least one local different string, wherein each of the local different string is an indicative of genetic difference between one sequence a string and one of the rests of the sequence strings among the plurality of sequence strings. Then, the method continues with determining a plurality of difference scores among the plurality of sequence strings from the plurality of local differential string sets. When a predetermined ratio of the plurality of different scores is under a predetermined threshold, the homogeneity of the plurality of the biological samples can be certified.

Still another aspect of inventive subject matter is directed towards a method of excluding an individual biological sample from a group of biological samples using sequencing data obtained from the biological samples. In this method, a plurality of local alignments are produced, using a sequence analysis engine, by incrementally synchronizing a plurality of sequence strings using a known position of at least one of plurality of corresponding substrings. The plurality of genetic sequence strings representing the plurality of biological samples, respectively, and the plurality of genetic sequence strings have a plurality of corresponding sub-strings. Then, using the plurality of local alignments, the sequence analysis engine to generate a plurality of local differential string sets among the plurality of sequence strings. Each of the plurality of local differential string sets comprises at least one local different string, wherein each of the local different string is an indicative of genetic difference between one sequence string and one of the rests of the sequence strings among the plurality of sequence strings. Then, the method continues with determining a plurality of difference scores among the plurality of sequence strings from the plurality of local differential string sets. The individual biological sample can be excluded as an outlier sample based on the differences between genetic distances of the individual biological sample with other biological samples and genetic distances among other biological samples.

In still another aspect of inventive subject natter, the inventors contemplate method of excluding an individual biological sample (or individual) from a group of biological samples (or individuals) using sequencing data obtained from the biological samples. In this method a plurality of local alignments are produced, using a sequence analysis engine, by incrementally synchronic ng a plurality of sequence strings using a known position of at least one of plurality of corresponding substrings. The plurality of genetic sequence strings representing the plurality of biological samples, respectively, and the plurality of genetic sequence strings have a plurality of corresponding sub-strings. Then, using the plurality of local alignments, the sequence analysis engine to generate a plurality of local differential suing sets among the plurality of sequence strings. Each of the plurality of local differential string seta comprises at least one local different string, wherein each of the local different string is an indicative of genetic difference between one sequence string and one of the rests of the sequence strings among the plurality of sequence strings. Then, the method continues with select a quality local different string from the local differential string set based on a distribution pattern of the local different strings. Preferably, the quality local differential string is present in at least 70% of sequence strings originated from the same biological sample. Then, from the quality local different string, a plurality of difference scores of the plurality of sequence strings is determined. Based on the different score of the individual biological sample (or individual), the individual biological sample (or individual) can be excluded from the group as an outlier sample.

Various objects, features, aspects and advantages of the inventive subject matter will become more apparent from the following detailed description of preferred embodiments with accompanied drawings presented herein.

BRIEF DESCRIPTION OF DRAWINGS

FIG. 3 illustrates an exemplar SAM/BAM file.

FIG. 7 depicts difference matrix for 10 Samples (log scale). The higher the number, the more dissimilar the two samples are from each other.

FIG. 8 depicts clustered difference matrix using sane data shown in FIG. 7. A total of 4 distinct dusters of samples were identified (A, B, C, D) from the batch of 10 samples.

DETAILED DESCRIPTION

Figure 1:
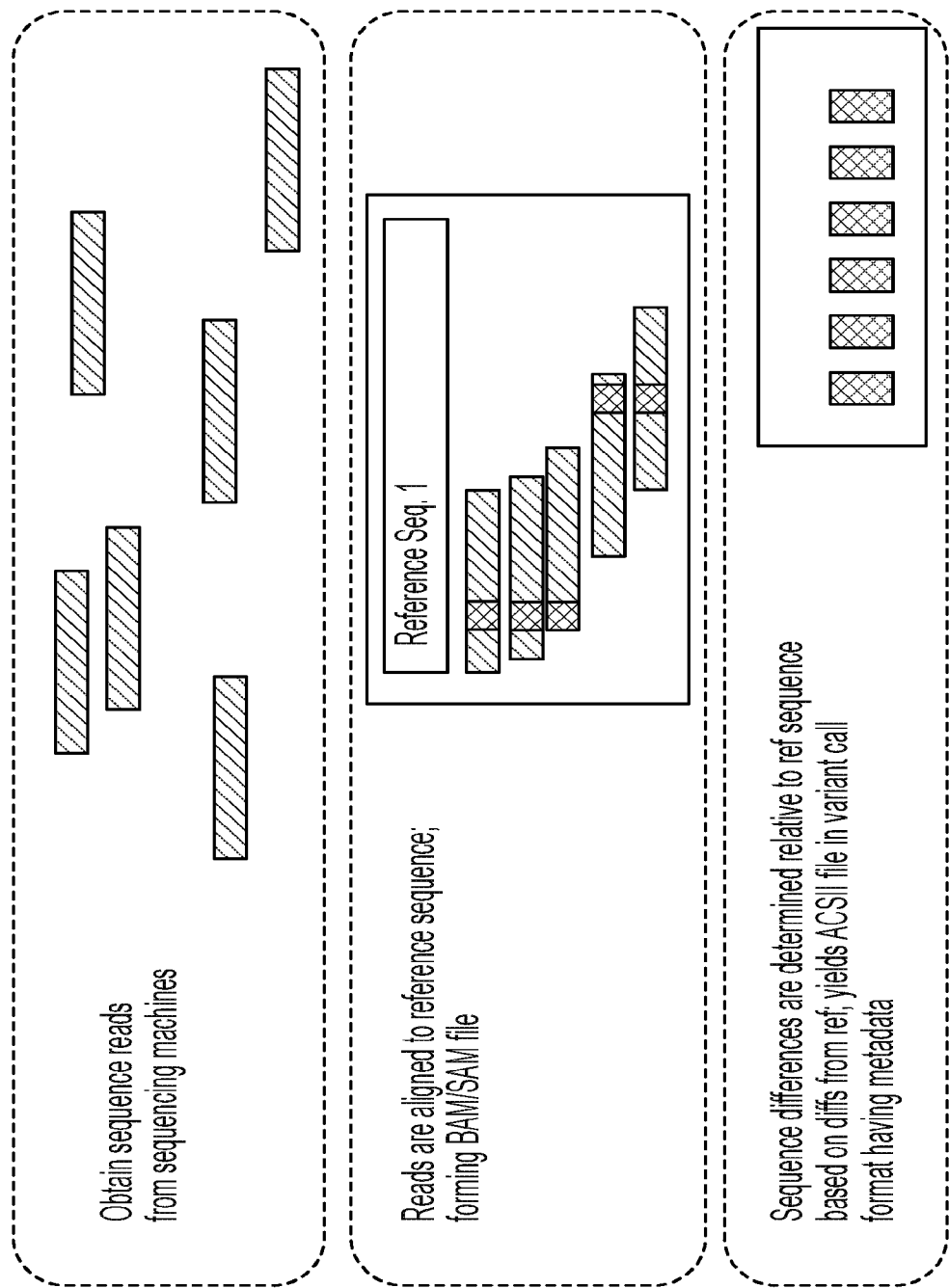
FIG. 1 shows a traditional method of genomic sequence analysis.

The inventors have discovered that omics data of a group of, preferably more than two, biological samples can be analyzed substantially simultaneously and effectively to determine the genetic distances from each other using parallel comparative analysis of high-throughput sequencing data. The inventors further discovered that such obtained genetic distances or differences among omics data of biological samples can be used to determine homogeneity of a group of biological samples and/or exclude an outlier sample to obtain highly homogeneous group of samples, which can be further used to achieve highly reliable and predictable treatment outcome to a drug or treatment regimen.

As used herein, the term "provide" or "providing" refers to and includes any acts of manufacturing, generating, placing, enabling to use, transferring, or otherwise making ready to use.

It should be noted that any language directed to a computer should be read to include any suitable combination of computing devices, including servers, interfaces, systems, databases, agents, peers, end, controllers, modules, cloud system, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or otherwise program the computing device to provide the roles responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, cloud systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet. LAN, WAN, VPN, or other type of packet switched network; a circuit switched network; cell switched network or other type of network.

As used in the description herein and throughout the claims that follow, when a system, engine, server, device, module, or other computing element is described as configured to perform or execute functions on data in a memory, the meaning of "configured to" or "programmed to" is defined structurally as one or more processors or cores of the computing element being programmed or otherwise manipulated or altered by a set of software instructions stored in the memory of the computing dement to execute the set of functions or operate on target data or data objects stored in the memory.

It should be appreciated that in traditional methods of analyzing multiple sequences, as shown in FIG. 1, raw read sequences are obtained from sequencing machines or databases, and are aligned to a reference sequence. Such alignment produces a SAM/BAM file. On that basis, the sequence differences from the reference sequence can then be identified in variant call format (*.vcf) to reduce rile size. In this approach, it must be recognized that the reference sequence is used to identify mutations in the sequence compared to a possible reference sequence. This, the sequence information in the SAM/SAM file and the subsequently formed vcf file is based on sequence differences from the reference sequence, not differences from other multiple sequences compared with each other.

Figure 2:
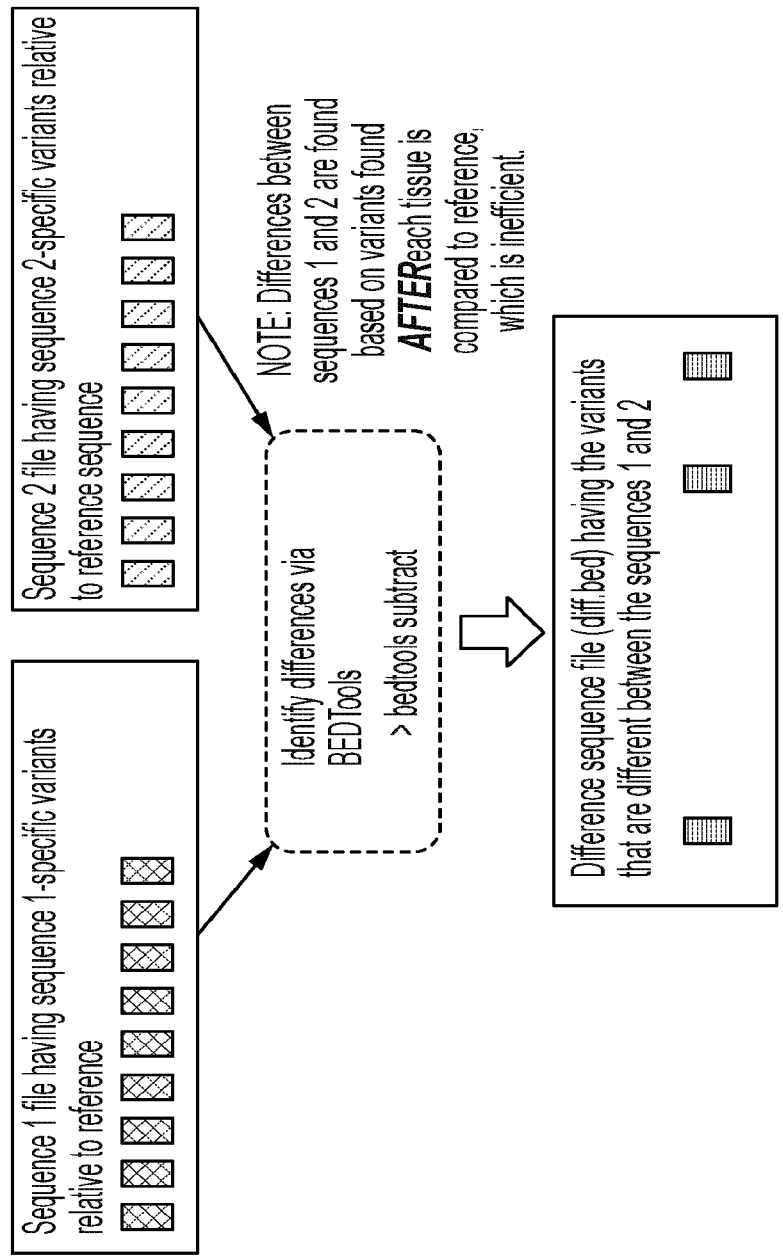
FIG. 2 illustrates a subsequent comparison of two genomic sequences using traditional method of FIG. 1.

FIG. 2 illustrates a subsequent comparison of the two sequences shown in FIG. 1, which is performed using BEDTools and the corresponding vcf files. In such approach, it should be appreciated that the vcf file for the sequence 1 and the vcf file for the sequence 2 are obtained via the process shown in FIG. 1. BEDTools then subtracts the sequence 2 vcf file from the sequence 1 vcf file by removing intervals based on overlaps between the two files. Therefore, it must be recognized that the differences in sequence information are found based on the complete sequences after each sequence information has been separately compared against a reference. Such comparison is highly inefficient and typically requires substantial memory allocation and/or computational effort for such operation.

Omics Data Analysis Using BAMBAM

BamBam is a computationally efficient method for surveying large sequencing datasets to produce a set of high-quality genomic events that occur within each biological samples (e.g. a cell, a tissue, an organism, a microorganelle, etc.). In other words, BamBam is a tool that simultaneously analyzes each genomic position from two different individuals or biological samples using the aligned short-read data contained in SAM/BAM-formatted files (SAMtools library; Li H, Handsaker B, Wysoker A, Fennell T, Ruan J, Homer N, Marth G, Abecasis G, Durbin R; 1000 Genome Project Data Processing Subgroup. The Sequence Alignment/Map format and SAMtools. *Bioinformatics.* 2009 Aug 15:25 (16):2078–9. Epub 2009 Jun. 8). BAMBAM is more fully described in U.S. Pat. Nos. 9,646,134; 9,652,587; 9,721, 062; and U.S. Pat. No. 9,824,181 to Sanborn at al. and all titled "BAMBAM: PARALLEL COMPARATIVE ANALYS1S OF HIGH-THROUGHPUT SEQUENCING DATA".

At the outset, and from a high-level perspective, it should be appreciated that a BAM file is the binary equivalent of a SAM file, and as such BAM and SAM files contain substantially exactly the same information simply stored in a different format. SAM riles are presented in their native text format (ASCII) to allow for readability by a human operator whole the BAM file is a binary, compact version of the SAM file. Moreover, while a single SAM/BAM rile contains multiple short sequence reads plus metadata as shown in more detail below, it must be recognized that the SAM/BAM file is organized as a tab delimited single file Consequently, it should be appreciated that SAM/BAM files often have very large files sixes, especially where whole genome sequencing at high oversampling rates produce such files. For example, a SAM file that includes a whole genome with 50× oversampling could easily be over 150 GB. It should be appreciated that, in some embodiments, massive oversampling can be used especially in scenarios where homogeneity of samples is expected. Thus, it is expected that, in some embodiments, some sequence riles could comprise 100×, 1000×, 10000×, or more oversampling. For example, when using the disclosed techniques in highly clonal organisms, a SAM file could contain 10000 reads per position. Such an approach is considered advantageous because it provides for discovering minute or subtle differences among the highly homogenous organisms, populations, or other sets of samples.

FIG. 3 shows an exemplary SAM/BAM file structure in which the first two lines are header information (preceded by @ that indicates 1) file format version (VN) 1.5, 2) the sorting order of the sequence reads in the file (SO) where reads are present in position order. 3) the type/identity of the reference sequence (SN) by name "ref", and 4) the length of the reference sequence (LN) 45 bane pairs.

Following the header are then the individual sequence reads with one read and associated metadata per line, here the reads are sorted according to their respective position relative to the reference sequence. It should thus be recognized that a SAM/BAM file includes 1) multiple reads (here: r001, r002, . . . ) with metadata for each read, and 2) each read has read specific metadata relative to a specific reference sequence (here: 'ref').

With respect to the metadata for each read, the publically available Sequence Alignment/Map Format Specification by the SAM/BAM Format Specification Working Group (https://samtools.github.io/hts-specs/SAMv1.pdf) provides detailed information. For example, the metadata that can be seen from Fib 3 includes as following:

Column 1 r001, . . . denotes the name/designation of the individual sequence read.

Column 2 99, . . . indicates a bitwise FLAG that provides specific indications for the read relative to the reference sequence (e.g. being reverse complemented).

Column 3 ref indicates the type/name of the reference sequence used.

Column 4 7, . . . indicates the position of the first base in the read relative to the first base of the reference sequence used. Note that the sequence reads are sorted in linear order relative to the reference sequence (as also indicated in the header SO field 'coordinate').

Column 5 30, . . . is a measure of mapping quality for the sequence read.

Column 6 8M2I . . . is a CIGAR string indicating the sequential match for the sequence mad relative to the reference sequence. For read r001 the string is 8M2I4M1D3M (first 8 bases match the reference, next two bases are an insertion to the reference, next 4 bases match the reference, net single base is a deletion from the reference, final 3 bases match the reference).

Column 7= is an identification of the ref. name of the next read.

Column 8 37, . . . is an identification of the position of the next read

Column 9 39, . . . is an indication of the observed Template Length

Column 10TTA . . . is the actual sequence read.

Column 11*, . . . is a quality identifier

Column 12SA . . . is an optional field related to the reed (e.g. SA indicates other canonical alignments in a chimeric alignment with further info).

Figure 4:
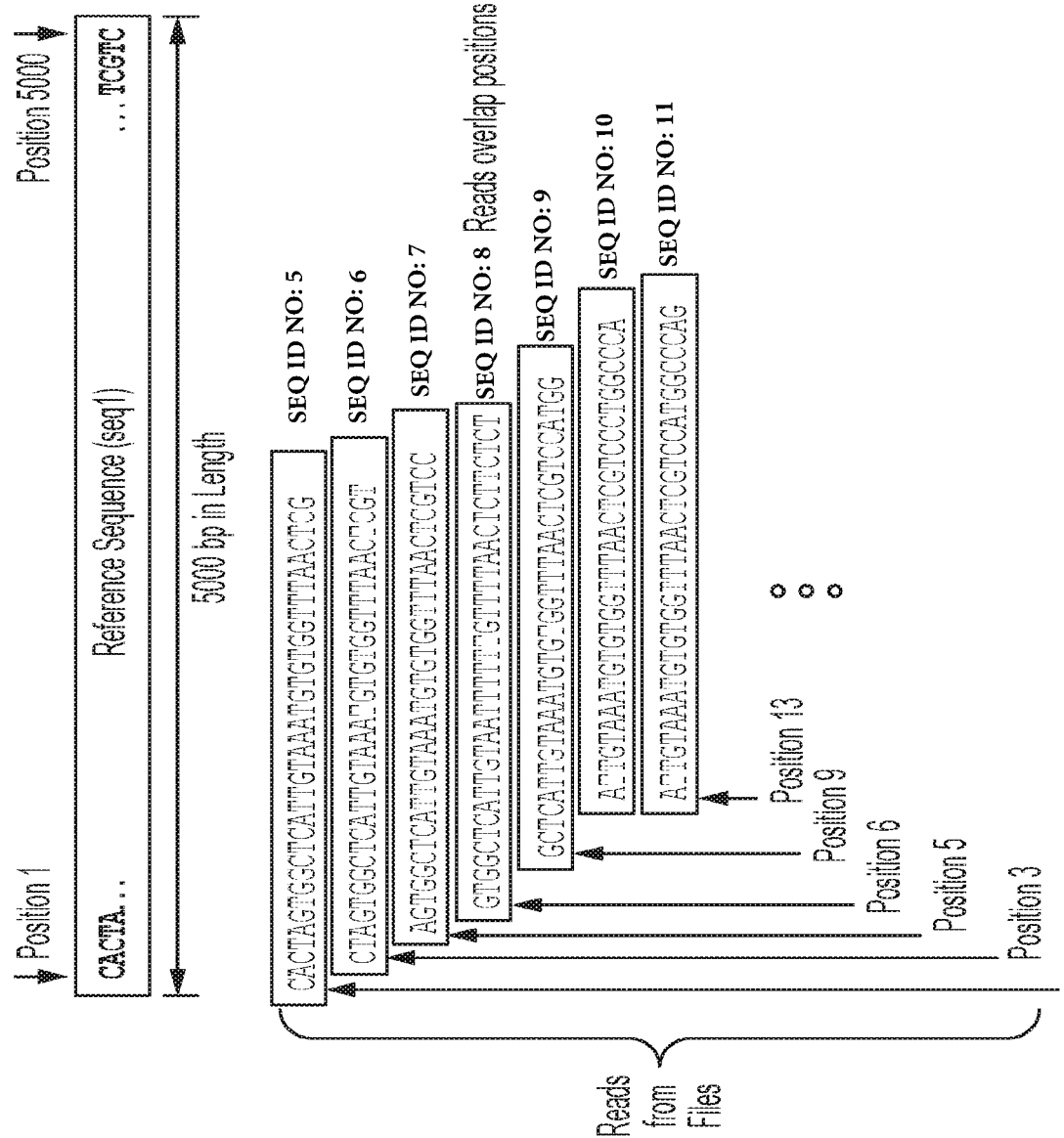
FIG. 4 schematically depicts an exemplary SAM/BAM file structure.

FIG. 4 provides a more simplified depiction of a SAM/BAM file. The SAM/BAM file is a single file that includes multiple and distinct sequence reads that can overlap each other with several annotations relative to a specified reference sequence (i.e., "ref"). Also, each single BAM file (regardless of its origin) contains metadata for each read relative to the same specific reference sequence. The reference sequence is a generic reference for position purposes and does not represent a biological sample sequence or any other genomic information from the biological sample. Thus, as shown in the example of FIG. 4, each single BAM file contains multiple reads overlapping and linearly aligned to a reference sequence. Although the previous discussion relates to SAM/BAM file formats, one should appreciate that other forms of genomic sequence formats are also contemplate including CRAM. FASTA, FASTQ, GAR, proprietary formats, or other formats.

The inventors contemplate that multiple genetic sequence strings obtained from multiple biological samples in SAM/BAM format that are aligned to a reference sequence can be further aligned to each other to determine genetic distances from each other. As used herein, the term "biological sample" refers any cell, tissue, or an organism (e.g., virus, bacteria, yeast, a mouse, a human, plants, fungi, single cell organisms, insects, planarians, exosomes of organisms, etc.), regardless of its health status, which contains genetic material (e.g. genomic DNA, cDNA, RNA, ctRNA, cfRNA, methylation data, etc.) or proteins. Thus, the biological sample may include cultured call lines, isolated cells, an organ, a bodily fluid (e.g. blood, cerebrospinal fluid, etc.), exosomes, lysate, or a whole animal. Although the examples provide reference to genome sequences, it should be appreciated that the inventors fully contemplate that the disclosed techniques can be applied in a similar fashion to specific regions of the "omics" constructs. For example, the similarity analysis can be applied to just coding regions of a genome rather than the whole genome. Other examples of specific "omics" constructs could include expression of specific peptides, specific genes and/or associated mRNA, mitochondrial DNA, epigenetic factors, or other areas of "omics" interest or relevance.

It is contemplated that the type of genetic sequence strings may vary considerably depending on the particular nature of analysis and samples, and may be nucleic acid sequences (DNA or RNA) as well as protein sequences. Most typically, however, the genetic sequence strings will be nucleic acid strings that will represent significant portions of the genome, transcriptome, and/or proteome of the first and second tissues under analysis. For example, it is contemplated that the first and second genetic sequence strings represent at least 10%, more typically at least 25% more typically at least 50% even more typically at least 70% and most typically at least 90% or even substantially the entire (at least 98%) genome, transcriptome or proteome of the first and second tissues. This, it should be appreciated that the systems and methods presented herein will allow for a rapid and highly comprehensive overview of significant differences between first and second tissues while producing a compact and informative output file.

Preferably, each genetic sequence strings have multiple relatively small genomic sequence sub-strings (for example, short reads from sequencing runs) that overlap with each other (e.g., each sub-string is 50 base pairs long that cover positions 1–50, 25–75.33–105, 95–145, 130–180, 170–220, respectively, etc.). In such embodiments, it is preferred that at least two sub-strings reads are overlapped for at least 5 base pairs, at least 10 base pairs, at least 15 base pairs, and collectively provide a read of at least 100 base pairs, at least 201) base pairs, at least 301) base pairs, or at least 501) base pairs. In some embodiments, even very long reads having over 1001) base pairs are leveraged. Such reads can be generated via devices such as the MinION® flow call offered by Oxford Nanopore®.

Figure 5:
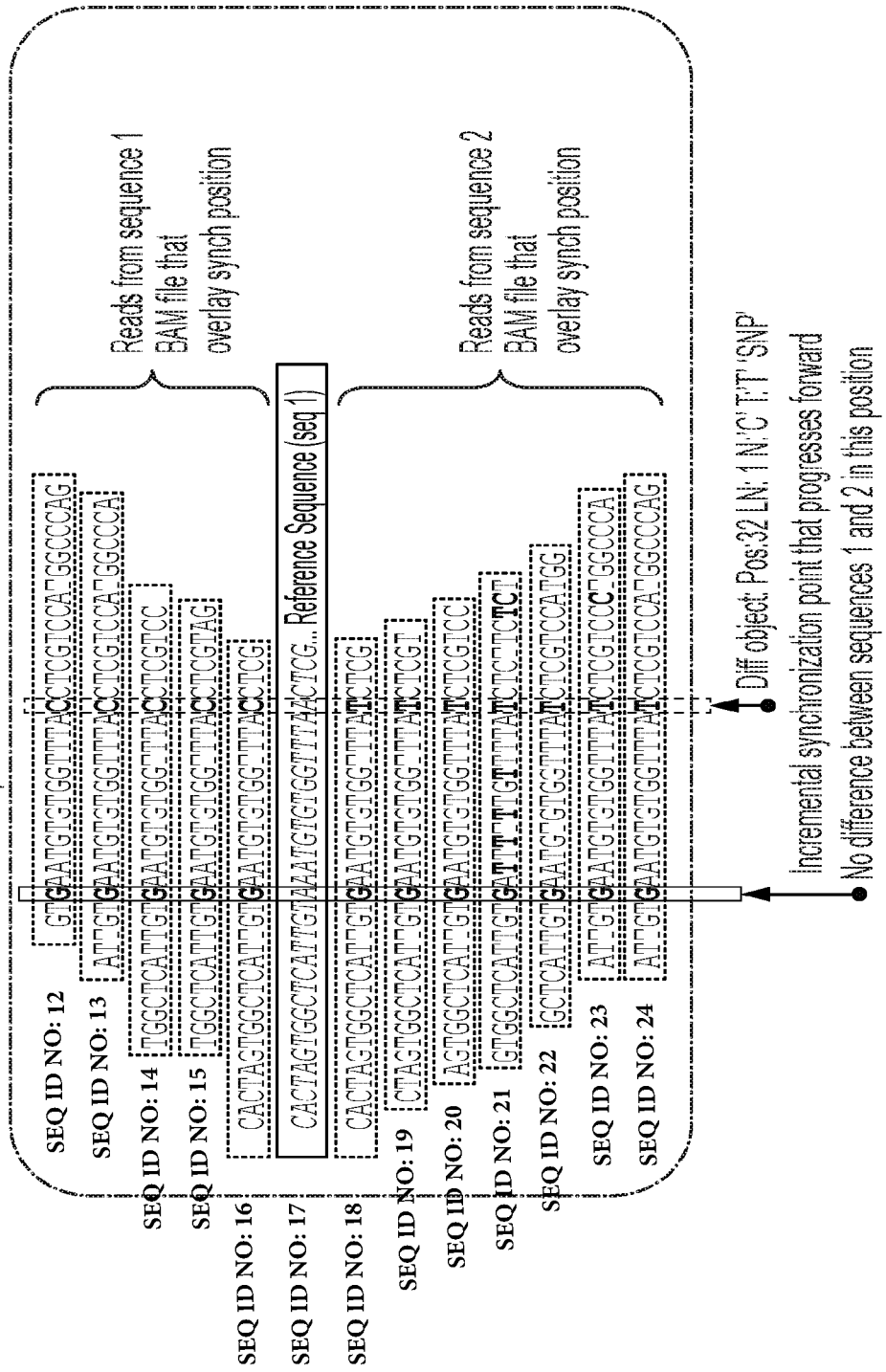
FIG. 5 illustrates multiple sequence alignments using synchronized reads.

In an especially preferred aspect of the inventive subject matter, which is depicted in FIG. 5 as a simplified example, multiple relatively small genomic sequence sub-strings (for example, short reads from sequencing rims) of larger genetic sequence strings from a first and second biological samples are obtained. In some embodiments, the genetic sequence strings can be directly obtained from a sequencing machine that is informationally coupled to a sequence analysis engine. In other embodiments, the genetic sequence strings that are obtained from the sequencing machine can be stored in a database that is informationally coupled to a sequence analysis engine. As used herein, the term "informationally coupled" database and sequence analysis engine means that the data stored in the database can be transmitted automatically or via user's request, possibly over a network, to the sequence analysis engine to so be processed by the sequence analysis engine.

The following discussion describes various actions taken by one or more computing devices. Although the actions and associated computational efforts are described with respect to an analysis engine, it should be appreciate that each individual action could be implemented as a separate computation tool or utility Such tools and/or utilities can then be combined in parallel or serially to create a full fledge workflow that meets the requirements of the described inventive techniques. The genetic sequence strings are then incrementally synchronized using one or more known positions of as least one of corresponding sub-strings to so produce a local alignment. The so generated local alignment is then compared to generate a local differential string between the first and second sequence strings within the local alignment. Thus, where the sequences strings are DNA or RNA sequences, the local differential string includes at least one nucleic acid sequence that is different between the first and second genetic sequence strings. The inventors contemplate that the length of the local differential string may vary depending on the differences between two sequences strings. Preferable, the length of the local differential string can be 1-to more than 1000 base pairs, 1–100 base pairs, preferably between 1–50 base pairs, more preferably between 1–20 base pairs.

In some embodiments, the alignment of two sequence strings may generate more than one local differential strings (i e, two or more unmatched, non-continuous nucleic acid sequences between two sequence strings). In such embodiments, multiple differential strings that represent sequence differences between two sequence strings can be grouped in the differential string set.

In some embodiments, the local differential string may comprise a block of nucleic acid sequence that is at least 10 base pairs, at least 50 base pairs, at least 100 base pairs, at least 500 base pairs. In these embodiments, it is preferred that at least 50%, 70%, at least 80%, at least 90% of base pairs in the local differential string differ between the two sequence strings. It is contemplated that such block form of local differential suing may provide more accurate assessment to determine genetic differences between two biological samples where the point mutation occurs at a high frequency in a localized manner (kataegis) or a clustered genomic rearrangement in a localized manner (chromothripsis). Further, such genomic rearrangements can be leveraged to identify samples have expression of similar fusions.

It should be recognized that instead of processing two extremely large files to generate another extremely large intermediate (or even output) file, genome wide analysis can be achieved in multiple significantly smaller portions wherein the smaller portions are aligned to a reference genome using known positions within the genome of one or more sub-strings. Viewed from another angle, alignment is performed by incremental synchronization of sequence strings using known positions of substrings and a reference genome sequence, and an output rile can be generated that comprises only relevant cages with respect to a reference genome. Thus, the processing speed is signifies improved and the amount of data required for production of a meaningful output is dramatically reduced. Still further, contemplated systems and methods further allow, inter alia, haplotyping/somatic and germline variant calling and determination of allele-specific copy numbers. Moreover, the systems and methods presented herein are suitable for use with sequence information in SAM/BAM-format.

For example, multiple sequencing fragments (for example, short reads from a tumor sample of a donor and corresponding non-tumor sample of the same donor) are aligned to the same reference genome, which is employed to organize the sequencing fragments from the samples. BAM-BAM then uses two or more sequencing fragment datasets (from two or more different biological samples) and reads the datasets such that all sequences in the two or more datasets overlapping the same genomic position (based on their position relative to the reference genome and annotation in sub-strings) are processed at the same time. This is the most efficient method for processing such data, while also enabling complex analyses that would be difficult or impossible to accomplish in a serialized manner, where each dataset is processed by itself, and results are only merged afterwards.

Consequently, it should be recognized that BAMBAM incrementally reads from two or more files, or data streams, at the same time, constantly keeping each BAM file in synchrony with the other(s) and piling up the genomic reads that overlap every common genomic location between the two files. For each of the pileups, BAMBAM runs a series of analyses before discarding the pileups and moving to the net common genomic location. By processing in this manner, the computer's RAM usage is dramatically reduced and processing speed is limited primarily by the speed that the file system can read the two or more files. This enables BAMBAM to process massive amounts of data quickly, while being flexible enough to run on a single computer or across a computer cluster. Another important benefit to processing these files with BAMBAM is that its output is fairly minimal, typically only including the important differences found in each file. This produces what is essentially a v(bole-genome differential analysis between two biological samples, requiring much less disk storage than it would take if all genome information was stored for each file separately.

Optionally, so obtained local differential suing(s) can be filtered and/or qualitatively evaluated for false positive change in the nucleic acid sequence by analyzing the distribution of the local differential string(s). For example, where biological samples 1 and 2 are sequenced to an average read depth of 30× (same base position covered by at least 30 reads), the sequence suing 1 and 2 obtained from biological samples 1 and 2, respectively, may contain 30 sub-strings that reads the same position (e.g. position 13 shown in FIG. 4) of the sequence string. Thus, where two sequence strings (sequence strings 1 and 2) are compared, at least or about 60 sub-strings (30 sub-strings each from sequence strings 1 and 2) have a sequence read on a given position of the sequence string. In such example, while the difference of a nucleic acid in a given position between two sequence strings is likely to reflect the difference between two sequence strings, any difference of a nucleic acid in a given position among the sub-strings in the same sequence string may be resulted from random sequencing error. Thus, a local differential string that has a variance in the reads among at least 10%, at least 20%, at least 30%, at least 50% of sub-strings of the same sequence string can be filtered and/or disregarded as a false-positive. Alternatively or additionally, a local differential string that is present in at least 10%, at least 20% at least 30% of sub-strings of both sequence strings can be filtered and/or disregarded as a false-positive. For example, where all sub-strings of sequence string 1 has T at position 13 and 60% and 40% of sub-strings of sequence string 2 has T and A at position 13, respectively, the differential string "A" at position 13 may be filtered and disregarded from further analysis. For other example, where 80% and 20% of sub-strings of sequence string 1 has T and A at position 13, and 80% and 20% of sub-strings of sequence string 1 has A and T, respectively, the differential string "A" at position 13 may be filtered and disregarded from further analysis. Therefore, depending on the desired thresholds, nucleotides may be counted as artifacts at low frequencies at a given position, as tonal or individual variant at a higher frequency, or as alleles at appropriate frequencies (e.g., 50% per sample). As discussed previously, in highly homogenous populations of organisms, it is expected that a larger number of reads may be necessary to generate a statistically significant identification of differences.

Variant Calling

Alternatively and/or additionally, the significance of the sequence change can be assessed via variant calling. Because BamBam keeps the sequence data in the pair of files in sync across the genome, a complex mutation model that requires sequencing data from both BAM files derived from two biological samples as well as the reference can be implemented easily. This model aims to maximize the joint probability of both sequence strings of two biological samples. To find the optimal genotypes of two sequence strings from two biological samples the inventors aim to maximize the likelihood defined by:

$$P(D_g, D_t, G_g, G_t | a, r) = P(D_g | G_g) P(G_g | r) P(D_t | G_g, G_t, a) P(G_t | G_g) \quad (1)$$

$$P(D_{1g}, a D_{1t}, G_{1g}, G_{1t} \dashv | a, r) = P(D_{1g} \dashv | G_{1g}) P(G_{1g} \dashv | r) P(D_{1t} \dashv | G_{1g}, G_{1t}, a) P(G_{1t} \dashv | G_{1g}) \quad (1)$$

where r is the observed reference slide, a the fraction of normal contamination, and the genotypes of sequence string 1 and 2 are defined by $Gt=(t_1, t_2)$ and $Gg=(g_1, g_2)$, respectively, where $t_1, t_2, g_1, g_2 \varepsilon \{A, T, C, G\}$. The sequence data of sequence string 1 and 2 are defined as a set of reads $D_t=\{d_t^1, d_t^2, \ldots, d_t^m\}$ and $D_g=\{d_g^1, d_g^2, \ldots, d_g^m\}$, respectively, with the observed bases $d_t^i$, $d_g^i \varepsilon \{A, T, C, G\}$. All data used in the model must exceed user-defined base and mapping quality thresholds.

The probability of the germline alleles given the germline genotype is modeled as a multinomial over the four nucleotides:

$$P(D_g | G_g) = \frac{n!}{n_A! n_T! n_G! n_C!} \prod_i^n P(d_g^i | G_g),$$

where n is the total number of germline reads at this position and $n_A, n_G, n_C, n_T$ are the reads supporting each observed allele. The base probabilities, $P(d_g^i)G_g)$, are assumed to be independent, coming from either of the two parental alleles represented by the genotype $G_g$, while also incorporating the approximate base error rate of the sequencer. The prior on the sequence string 1 genotype is conditioned on the reference base as:

$$P(G_g|)r=a)=\{\mu_{aa}, \mu_{ab}, \mu_{bb}\}$$

where $\mu_{aa}$ is the probability that the position is homozygous reference, $\mu_{ab}$ is heterozygous reference, and $\mu_{bb}$ is homozygous non-reference. At this time, the sequence string 1 prior does not incorporate any information on known, inherited SNPs.

The probability of the set of sequence 2 reads is again defined as multinomial $$P(D_t | D_t, G_g, \alpha) = \frac{n!}{n_A! n_T! n_G! n_C!} \prod_i^n P(d_g^i | G_t, G_g, \alpha),$$

where m is the total number of germline reads at this position and $m_A, m_G, m_C, m_T$ are the reads supporting each observed allele in the sequence 2 dataset, and the probability of each sequence 2 read is a mixture of base probabilities derived from both sequence 2 and sequence 1 genotypes that is controlled by the fraction of normal contamination, a, as $$P(d_t^i | G_t, G_g, a) = a P(d_t^i | G_t) + 1 - a) P(d_t^i | G_g)$$

and the probability of the sequence 2 genotype is defined by a simple mutation model from an the sequence 1 genotype $$P(G_t | G_g) = \max[P(t_1 | g_1) P(t_2 | g_2), P(t_1 | g_2) P(t_2 | g_1)].$$

where the probability of no mutation (for example, t1=g1) is maximal and the probability of transitions (that is, A→G, T→C) are four times more likely than transversions (that is, A→T, T→G). All model parameters, a, μaa, μab, μbb, and base probabilities, P(di|G), for the multinomial distributions are user-definable.

The sequence 2 and 1 genotypes, Gt max, Gg maxi, selected are those that maximize (1), and the posterior probability defined by $$\frac{P(D_g, D_t, G_g^{max}, G_t^{max} | \alpha, r)}{\sum_{i,j} P(D_g, D_t, G_g = i, G_t = j | \alpha, r)}$$

can be used to score the confidence in the pair of inferred genotypes. If the sequence 2 and sequence 1 genotypes differ, the mutations in sequence 2 will be reported along with its respective confidence.

Maximizing the likelihood of one or both sequence 1 and 2 genotypes helps to improve the accuracy of both inferred genotypes, especially in situations where one or both sequence datasets have low coverage of a particular genomic position. Other mutation calling algorithms, such as MAQ and SNVMix, that analyze a single sequencing dataset are more likely to make mistakes when the non-reference or mutant alleles have low support (Li, H., et al. (2008) Mapping short DNA sequencing reads and calling variants using mapping quality scores, Genome Research, 11, 1851-1858; Goya, R. et al. (2010) SNVMix: predicting single nucleotide variants from next-generation sequencing of tumors, Bioinformatics, 26, 730–736).

In addition to collecting allele support from all reads at a given genomic position, information on the reads are collected (such as which strand, forward or reverse, the read maps to, the position of the allele within the read, the average quality of the alleles, etc.) and used to selectively filter out false positive calls. We expect a random distribution of strands and allele positions for all of the allele supporting a variant, and if the distribution is skewed significantly from this random distribution (that is, all variant alleles are found near the tail end of a read), then this suggest that the variant call is suspect.

It is also contemplated that the variant calling for sequence changes can be also performed by other analysis tools, including, but not limited to, MuTect (*Nat Biotechnol.* 2013 Mar; 31(3):213-9), MuTect2, HaploTypeCaller, Strelka2 (*Bioinformatics*, Volume 28, Issue 14, 15 Jul. 2012, Pages 1811–1817) or other genomic artifact detection tool.

Difference Score and Genetic Distance

The inventors further contemplate that the local differential string or the local differential string set can be further analyzed to determine the difference score between two sequence strings. Preferably, each local differential string can be analyzed to determine functional attributes, including its functional location (e.g., axon, intron, regulatory element, untranslated region, etc.), relation to types of mutations (e.g., a missense mutation, a nonsense mutation, an insertion, a deletion, a duplication, a frameshift mutation, a neat expansion, etc.) resulted from the local differential string, numbers of mutations in the local differential string frequency of mutations in the local differential string (especially where the local differential sting is a block of nucleic acid sequence), and other status changes of genome (e.g. at least one ploidy, gene copy number, repeat copy number, insertion of viral genes, transposition, lose of heterozygosity, etc.). In some embodiments, each local differential string can be further analyzed to determine the biological sample's status with respect to signaling pathways (e.g., growth factor signaling pathway, a transcription factor signaling pathway, an apoptosis pathway, a cell cycle pathway, and a hormone response pathway, etc.).

Based on the functional attributes of the local differential string(s) and/or pileup information and associated pileup metadata, a difference score can be determined for each of local differential string(s). While the difference score can reflect a single attribute of the local differential string(s), it is generally contemplated that the difference score is typically a compound score reflecting a plurality of attributes of the local differential string(s). For example, the local differential string has one nucleic acid change between sequence strings 1 and 2, and the single nucleic acid change can result nonsense mutation in exon 3 of gene A that can be dominant negative factor for signaling pathway B. In such example, the difference score can be determined by combining sub-scores for number of mutation (1, one nucleic acid change), the type of mutation (nonsense mutation), location of mutation (exon 3), and physiological impact (dominant negative factor for signaling pathway B). For other example, the local differential string has two nucleic acids change between sequence strings 1 and 2, and such change does not result in any mutation of encoded protein C, yet night affect the expression level of protein C. In such example, the difference score can be determined by combining sub-scores for number of mutations (2) and the physiological impact (the expression level of protein C).

As different types of mutations and their locations may have different physiological impact, it is contemplated that different types of mutation weigh differently. For example, a nonsense mutation, a frameshift mutation, a chromosomal inversion or a deletion can weigh at least 5 times, at least 10 times higher than a silent mutation. Further, any mutation in the coding area of a gene (e.g., exon) can weigh higher than any mutation in the non-coding pseudogene. Thus, weight of each mutation can be determined based on its significance to the physiological impact, in some scenarios the weight could even be zero if the mutation is not relevant to the core goals of the analysis.

It is also contemplated that, in some embodiments, where the local differential string set includes multiple local differential strings, the difference score can be determined by collectively considering the relationship of multiple local differential strings. For example, where the local differential string set includes four local differential strings which are independent with each other with respect to physiological impact, the difference score may be determined by sum of individual difference scores of four local differential strings. In another example, where the local differential string set includes four local differential strings and two local differential strings result in same functional change in the same gene or one local differential string nulls the physiological impact of the another differential string (e.g., both differential strings are present in the same gene: one is nonsense mutation and another r is a frameshift mutation present at downstream of the nonsense mutation), then one of the two differential strings may not be considered in determining the difference score.

The inventors further contemplate that so obtained difference score between two sequence strings (derived from two or more biological samples and possibly associated pileups at overlapping positions of the strings) can be used to determine a genetic distance between the two biological samples. As used herein, a genetic distance between two biological samples refers a relative genetic similarity calculated by similarity of nucleic acid sequences, preferably genetic similarity with respect to expected phenotypes (e.g., mRNA end/or protein expression level, function of expressed proteins, signaling pathways etc.) of two biological samples. Thus, in some embodiments, the genetic distance can be directly proportional to the difference score (e.g., same as difference score, proportional to the square of difference score, etc.). In other embodiments, a genetic distance can be determined based on a pro-determined threshold value of the difference score Preferably, the pre-determined threshold value of the difference score is a maximum score that the genetic variance of one biological sample may not render a measurable phenotypical difference from another biological sample. In these embodiments, a genetic distance between two biological samples may be determined "0" or "none or substantially none" or "identical" if the difference score is below the pre-determined threshold value. In addition, when the difference score is above the pre-determined threshold value, the genetic distance can be determined based on the difference between the difference score and the pro-determined threshold value. For example, a threshold value of the difference score can be pre-determined to 3.0 and the difference score between biological sample A and B is 2.5, then it can be determined that the genetic distance between biological sample A and B is "0" or "none or substantially none", thus genetically substantially identical. For other example, a threshold value of the difference score can be pre-determined to 3.0 and the difference score between biological sample A end B is 45, then the genetic distance between biological sample A and B can be determined based on the difference (4.5–3.0) between the threshold and the difference score. It should be appreciated that the differences score can be calculated as a function from a high dimensional space where each dimension represents different aspects of the "omics" data Consider that the dimensions of relevant could include multiple desirable features associated with clones. Example features might include coding regions of DNA, mRNA showing that the coding regions are expressed, and mitochondrial DNA. In such a scenario, there would likely be three dimensions of relevant. Thus the difference score could be calculated as a function over a set of one or more Euclidian distances between specific "omics" features among the biological samples.

In some embodiments, the genetic distances between two biological samples can be further compared to determine the homogeneity of a group of samples Preferably, the group of samples includes at least 3, at least 5, at least 10, at least 20, at least 50, at least 100 sequence strings originated from at least 3, at least 5, at least 10, at least 20, at least 50, at least 100 biological samples, respectively. The difference scores of each sequence string with the other sequence strings can be obtained by incrementally synchronizing each sequence string with the other sequence strings and generating a local differential string set for each pair of sequence strings (e.g., sequences A and B, sequences B and C, sequences A and C, etc.) as described above. It is contemplated that the a group of samples can be determined homogeneous or substantially homogeneous if the genetic distances between at least 85%, preferably at least 90%, more preferably at least 95% of biological samples are below the pre-determined threshold value.

Although percentages are given as an example, it should be appreciated that other measures are also contemplated. In some embodiments, similarity can be measures based on a measure of standard deviations relative to a baseline, a sum of logs of inferred genotype difference likelihoods, or other measures. In embodiments, where difference scores or similarity measures comprise two or more values or dimensions of relevance, thresholds can take on the form of contours. For example, in case that samples are genetically closely related, the frequency of local different strings may have less than 1 bp unmatched sequence per 1 Kb, per 10 Kb, per 100 Kb, 1 Mb, or 10 Mb length of the sequence strings. In such examples, the difference scores or similarity measures can be $1/10^3$, $1/10^4$, $1/10^5$, $1/10^6$, $1/10^7$ (corresponding to 1 bp/1 Kb, 1 bp/10 Kb, etc.), which can be convened into a logic scale as $-3$, $-4$, $-5$, $-6$, and $-7$. In such example, the homogeneity of a group of samples can be determined by comparing the average and/or median of difference scores in a log scale with pre determined threshold (e.g., $-6$, etc.). Of course, it should be noted that such measure and the threshold may be flexible depending on the scale of the genomic comparison. For example, where the similarity measure is performed in a scale of a gene or an exome, the difference score based on the log scale (number of unmatched base pairs per number of base pairs in the sequence string) can be higher than when the similarity measure is performed in a scale of a chromosome or an entire genome.

In addition, the homogeneity of a group of biological samples can be determined by comparing a standard deviation of the difference scores (preferably in slog scale) with respect to the average/median difference score. In such example, even if the median or average difference score may fall under the threshold, the distribution of the difference scores may indicate heterogeneity of the biological samples. Thus, in the embodiments where the difference scores are measured in a log scale, the homogeneity of a group of samples can be determined when the standard deviation of the difference scores is less than 0.5, less than 0.3, less than 0.1, etc.

Additionally, the genetic distances between two biological samples can be further compared to select an outlier sample from a group of biological samples. In some embodiments, the outlier sample can be selected based on the threshold value of the difference score. For example, the threshold value of difference score can be set as 4.0, and difference scores of biological sample G with respect to at least 85%, preferably at least 90%, more preferably at least 95% of other biological samples are above 4.0, then the biological sample G can be considered an outlier and can further be excluded from the group. In other embodiments the outlier sample can be selected based on the differences in genetic distances. For example, the threshold value of difference score can be set as 4.0 and genetic distances between any given pairs of biological samples can be determined based on the difference between their difference scores or similarity measures and the threshold value. In such example, a biological sample can be considered outlier and can further be excluded from the group if the average genetic distances of the biological sample with other biological samples are at least 30%, preferably at least 50% more preferably at least twice, most preferably at least 5 times farther than the average genetic distances among other biological samples. Alternatively, in other embodiments, a biological sample can be considered outlier and can further be excluded from the group if the difference between the median/average difference scores of the samples and the difference score of the biological sample is at least 30%, preferably at least 50% more preferably at least twice, most preferably at least 5 times larger than the predetermined threshold or the standard deviation of the difference scores.

While FIG. 4 depicts an example of aligning two sequence strings, each having multiple sub-strings, it should be appreciated that multiple sequence strings, each having multiple sub-strings, can be aligned all together to produce a local alignment for each sequence string. For example, five sequence strings (sequences 1-5), each having at least 30 sub-strings, can be aligned with respect to the reference sequence to generate local alignments for each sequence string. In such example, so generated local alignments are then compared with each oilier to generate a local differential string having at least one nucleic acid sequence that is not commonly shared among all sequence strings. For example, the local differential string may have a nucleic acid sequence G that is present in sequence string 5, where sequence strings 1-4 commonly has T in the same position. For other example, the local differential string may have a nucleic acid sequence G/C that is present in sequence string 4 and 5, respectively, where sequence strings 1-3 commonly has T in the same position. This, the local differential string may comprise any base pair change that is not commonly shared among the sequence strings.

Optionally, so obtained local differential string(s) can be filtered and/or qualitatively evaluated for false positive change in the nucleic acid sequence by analyzing the distribution of the local differential string(s). In some embodiments, it is assumed that the biological samples in the group are genetically closely related such that at least 80%, at least 90%, at least 95% of the biological samples share at least 90%, at least 99%, at least 99.90, or at leant 99.99% of genomics sequences. In other words, the biological samples are so closely related such that the samples may have, in average, less than 1 bp unmatched sequence per 1 Kb, per 10 Kb, per 100 Kb, 1 Mb, or 10 Mb. Thus, it is assumed that at least 90% more preferably at least 95%, more preferably at least 99% of such closely related biological sample may share the sane sequence at a given location. In such embodiments, a local differential string that has a variance in the reads among at least 10%, at least 20%, at least 30% at least 50% of sub-strings of the same sequence string can be filtered and/or disregarded as a false-positive. Alternatively and/or additionally, a local differential string that are present in at least 10%, at least 20%, at least 30% of sub-strings of more than 20%, preferably more than 30% of sequence strings of the group can be filtered and/or disregarded as a false-positive. Thus, when the local differential string(s) are filtered and/or qualitatively evaluated as above, the local differential string(s) represents a sequence difference (e.g., mutation, etc.) consistently (non-randomly) shown and present in a minority number (e.g., less than 20%, less than 10%, etc.) of biological samples.

Thus, in some embodiments, the local differential strings) can be identified as sequence variance of one sequence string over the majority of closely related sequence strings. In such embodiments, the local differential string(s) is sequence string-specific that may not be shared with other sequence strings. In other embodiments, the local differential string(s) can be identified as overall sequence variance(s) detected in the sequence strings of entire or at least a portion of the group of biological samples. For example, where the group includes 100 biological samples (having 100 corresponding sequence strings) and sequence string number 1, 43, 47, 70, and 99 includes one or two single base pair mutations (e g., mutations of sequence string number 1 at locations 237, 288, sequence string number 43 at locations 237, 244, sequence string number 47 at locations 244, sequence string number 70 at location 133, sequence string number 99 at location 320), then the overall local differential string set may include S local differential strings (at locations 133, 237, 244, 288, and 320).

The inventors further contemplate that the local differential string or the local differential string set can be further analyzed to determine the difference score or similarity measure of the biological sample. It should be appreciated that as the local differential string(s) are generated as a difference compared to overall and generally conserved sequences of the biological sample of the group, each sequence string may have corresponding local differential strings) that reflects relative genetic differences from the rest of the biological samples. As described above, each local differential string can be analyzed to determine functional attributes (e.g., functional location, status changes of genome, biological sample's status with respect to signaling pathways etc.), and attributed to a difference score based on such functional attributes.

As such, the difference scores of the biological samples can be further used to determine and/or certify the homogeneity of the group of biological samples. In some embodiments, the group of biological samples can be determined homogeneous or substantial) homogeneous if the difference scores of the at least 90%, preferably at least 95%, more preferably at least 99% of biological samples are below a pre determined threshold value. Again, the pre-determined threshold value of the difference score is a maximum score that the genetic variance of one biological sample may not render a measurable phenol pied difference from another biological sample or other biological samples generally in the group. Also, again, it should be appreciated that other measures am also contemplated. In some embodiments, similarity can be measures based on a measure of standard deviations relative to a baseline, a sum of logs of inferred genotype difference likelihoods, or other measures. In embodiments, where difference scores or similarity measures comprise two or more values or dimensions of relevance, thresholds can take on the form of contours. For example, in case that samples are genetically closely related, the frequency of local different strings may have less than 1 bp unmatched sequence per 1 Kb, per 10 Kb, per 100 Kb, 1 Mb, or 10 Mb length of the sequence strings. In such examples, the difference scores or similarity measures can be $1/10^3$, $1/10^4$, $1/10^5$, $1/10^6$, $1/10^7$ (corresponding to 1 bp/1 Kb, 1 bp/10 Kb, etc.), which can be converted into a log scale as −3, −4, −5, −6, and −7 In such example, the homogeneity of a group of samples can be determined by the difference score in a log scale with pro-determined threshold (e.g. −6, etc.). Of course, it should be noted that such measure and the threshold may be flexible depending on the scale of the genomic comparison. For example, where the similarity measure is performed in a scale of a gene or an exome, the difference score based on the log scale (number of unmatched base pairs per number of base pairs in the sequence string) can be higher than when the similarity measure is performed in a scale of a chromosome or an entire genome.

In addition, where the differential strings are identified as sequence variances) of individual sequence string over all other sequence strings or majority of sequence strings, the homogeneity of a group of biological samples can be determined by comparing a standard deviation of the difference scores (preferably in a log scale) with respect to the average/median difference score. In such example, even if the median or average difference score may fall under the threshold, the distribution of the difference scores may indicate heterogeneity of the biological samples. Thus, in the embodiments where the difference scores are measured in a log scale, the homogeneity of a group of samples can be determined when the standard deviation of the difference scores is less than 0.5, less than 0.3, less than 0.1, etc.

In other embodiments, so obtained difference scores of sequence strings of corresponding biological samples can be used to determine genetic distances among the biological samples, or the relative genetic distance of a biological sample from majority of other biological samples, which then can be used to determine and/or certify the homogeneity of the group of biological samples. In one embodiment, the genetic distance of a sequence string can be determined by the difference between the difference score of the sequence string and the median difference score of the sequence strings in the group. In another embodiment, the genetic distance of a sequence string can be determined by the difference between the difference score of the sequence string and the average difference score of the sequence strings in the group. The inventors contemplate that the group of biological samples can be determined homogeneous or substantially homogeneous if the genetic distances of the at least 90%, preferably at least 95%, more preferably at least 99% of biological samples are below a pre-determined threshold value.

Additionally, the difference scores and/or genetic distances of the sequence strings (of corresponding biological samples) can be further used to select an outlier sample from a group of biological samples. In some embodiments, an outlier sample can be selected based on the threshold value of the difference score. For example, the threshold value of difference score can be set as 4.0, any biological sample(s) that has difference score over 4.0 can be considered an outlier sample and be excluded from the group. In other embodiments, an outlier sample can be selected based on the threshold value of the difference score. For example, the threshold value of genetic distances can be set as 1.5, and any biological sample(s) that has difference score over 1.5 can be considered an outlier sample and be excluded from the group. In still other embodiments, the outlier sample can be selected based on average or median genetic distances of biological samples in the group. For example, a biological sample can be considered outlier and can further be excluded from the group if the genetic distance of the biological sample is at least 30%, preferably at least 50%, more preferably at least twice, most preferably at least 5 times farther than the average genetic distances of the biological samples in the group. Alternatively, in other embodiments, a biological sample can be considered outlier and can further be excluded from the group if the difference between the median/average difference scores of the samples and the difference score of the biological sample is at least 30%, preferably at least 50%, more preferably at least twice, most preferably at least 5 times larger than the predetermined threshold or the standard deviation of the difference scores.

Further, in some embodiments where the local differential string(s) can be identified as overall sequence variance(s) detected in the sequence strings of entire or at least a portion of the group of biological samples, an outlier sample can be identified by determining the distribution of the local differential string(s) among the sequence strings. For example, if one sequence string includes more than 50%, preferably more than 70%, more preferably more than 90% of local differential strings, such sequence string can be determined as an outlier and can further be excluded from the group.

The above described method of analyzing multiple omics data of multiple biological samples has a substantial technical effect in that it substantially reduces resource requirements (e.g., processing time and memory allocation) by producing local alignments among multiple sequence strings using a common reference sequence used only for positional information and synchronization. Such is achieved by incrementally synchronizing multiple sequences using the same reference sequence on a position-by-position basis. Viewed from a different perspective, processing of the multiple sequences occurs at the same time in memory using the same reference sequence. As such, the reference sequence information is only used for alignment of multiple sequences at the same time but not for determination of sequence changes among multiple sequences. As all individual sequencing reads in both sequence files are already aligned to the same reference sequence, a local differential string can be quickly calculated for the local alignment.

It should be also appreciated that numerous advantageous consequences arise from above described method. First, due to the local alignment, only minimal memory space is required to perform the analysis because only the reads that overlap the current synchronisation position are stored in memory, and due to the synchronous use of the same reference sequence during local alignment, true variations (not including false positive or false negative) are immediately apparent without the need for a subsequent secondary alignment Still further, as the local alignment is performed for all of multiple sequences, allele-specific variations can be immediately identified and assigned to all and individuals o multiple sequences.

Additionally, the inventors contemplated that the determination of homogeneity of group of biological samples can be performed periodically to the group of samples and/or the offspring group of samples (e.g., cell lines over several passages, offspring of animals, offspring seeds, done lines of thoroughbred animals, etc.) to determine whether homogeneity can be maintained in the group of samples over time or over the generations. For example, a group of tumor cell line derived from the same type of tumor of a patient can be maintained over at least 10 passages, over 20 passages, over 50 passages, or over 100 passages in three different culture conditions (e.g., different media compositions, cell splitting conditions, etc.). The homogeneity of the cell lines can be determined by every 3 passages, every 5 passages, every 10 passages, or every 20 passages. From such homogeneity test, one can confirm that the cell line is stably maintained without generating spontaneous mutations in the cell genome, or one can evaluate effect of different culture conditions to generate spontaneous mutations in the cell genome.

The inventors further notes that such similarity measure (homogeneity determination) can be further used in various biological and/or pharmaceutical fields. For example, multiple batches of genetically modified yeast that can increase the efficiency of wine or beer fermentation can be tested for their genetic homogeneity among the batches and/or additionally with the original batch of the yeasts to ensure the consistent quality of the yeasts before the genetically modified yeasts are provided to the market. For other example, genetically engineered mice (e.g., transgenic, knockout, knockin, etc.) can be tested for their genetic homogeneity among the mice of same generations or with prior generation of such mice before the mice are used as an experimental model of a disease study. For still other example, genetically engineered plant seeds can be tested for their genetic homogeneity among the batches of the seeds to ensure the quality of the seeds Additionally, such homogeneity test for genetically engineered plant seeds can be used to capture unauthorized multiple-generational use of the genetically engineered plant seeds by determining the homogeneity of the genetically engineered plant seeds with the seeds obtained from the farm (e.g., after at least two life cycles of the plants).

Thus, the similarity measure or the homogeneity test can be used as an intermediate step in a workflow for producing various products that require or prefer homogeneity among the products. Such products may include, but not limited to, pharmaceutical compositions (e.g., therapeutic cells, vaccines using genetically modified virus, yeast, or bacteria), foods (e.g., yeasts for wine fermentation, genetically modified crops, etc.), thoroughbred cloned animals (e.g., sheep, horses, bulls, dogs, cats, etc.) or cells or animals for laboratory use or clinical trials. For example, the therapeutic calls expressing heterologous protein can be generated by infecting virus having a recombinant nucleic acid encoding the heterologous protein. Batches of such generated therapeutic cells for each production can be evaluated qualitatively for their genetic homogeneity such that any non-homogeneous batches of therapeutic cells due to spontaneous mutations or any other types of unexpected genetic modifications (e.g., unexpected insertion in the host chromosome, etc.) can be excluded before the therapeutic cells are administered to the patients. Also, such procedure can be a part of quality control/troubleshooting step of mass production of therapeutic cells by identifying the most ideal or suitable conditions to maintain the homogeneity. Still further the similarity measures can be with respect to one or more dimensions of relevance. In the use of one thoroughbred animals, it is possible the mitochondrial DNA similarity is mare desirable than say generic identify because stamina of the animal might be more critical than phenotypic features. On the other hand, genomic identify with respect to genes relating to developing muscle tissue might override mitochondrial DNA similarity for food animals.

EXAMPLES

Example 1: Pairwise Difference Scores

The difference score $D_{ab}$ between a pair of samples a & b (over n elements) can be formulated genetically as a weighted average.

$$D_{ab} = \frac{\sum_{i=0}^{n} w(i) d_{ab}(i)}{\sum_{i=0}^{n} w(i)},$$

where w(i) is a per-element weighting factor and $d_{ab}(i)$ is a per-element difference score.

The weighting factors, w(i), can weight a subset of elements higher than others (i.e. w(i)>w(j)) or remove specific elements from the calculation altogether (i.e. w(i) =0), enabling the difference score to be adjusted to highlight differences in particular areas of interest. Examples of the weighting factors may include the following:

Exonic-Only Difference (where element i represents a position in the human genome):

$$w(i) = \begin{cases} 1 & \text{if } i = \text{exonic position} \\ 0 & \text{otherwise} \end{cases}$$

Genes-of-Interest-Only Difference (where element i represents a human gene):

$$w(i) = \begin{cases} 1 & \text{if } i = \text{gene of interest} \\ 0 & \text{otherwise} \end{cases}$$

Disruptive Variants Difference (where element i represents a detected variant):

$$w(i) = \begin{cases} 1.0 & \text{if } i = \text{nonsense or frameshift indel} \\ 0.5 & \text{if } i = \text{missense or in-frame shift indel} \\ 0.0 & \text{otherwise} \end{cases}$$

Similarly, the per-element difference scares compare a metric for a particular element measured in two samples a & b. Examples of difference scores may be include, but not limited to, the following:

Variant Allele Fraction (where element I represents a position in the human genome, and AF represents the allele fraction of each base (A, C, G, T) at that position).

$$d_{ab}(i) = \sum_{j=A,C,G,T} \text{abs}\left(AF_a^j(i) - AF_b^j(i)\right)$$

Gene expression difference (where element i represents a gene, and EXP represents a measure of gene expression, e.g. TPM, FPKM, relative gene coverage, etc.):

$$d_{ab}(i) = \text{abs}(EXP_a(i) - EXP_b(i))$$

Microsatellite instability (where element i represents a single microsatellite locus, and MS represents a count of the different numbers of repeats at the locus, a measure of the site's instability):

$$d_{ab}(i) = \text{abs}(MS_a(i) - MS_b(i))$$

Once a difference scone and weighting factor is established for a given test, the maximum allowed difference score can be determined via real or simulated data. This maximal difference can be used to flag samples that are too dissimilar (e.g. high contamination, mutational drift within gene(s) of interest, etc.).

Example 2: Allele Fraction Differences to Detect Sample Contamination

The experiment compares two simulated samples S1 and S2. Each sample consists of 10,000 genomic positions, where each position is defined by a genotype of two alleles a1 & a2, where a1 and a2 are randomly chosen from the set (A, C, G, T). When a1=a2, the site is homozygous for the allele a1/a2 When a1 and a2 differ, the site is heterozygous.

S2 is further defined as a mixture of sample S1 and an unrelated sample S3 (e.g. the contaminating samples). The degree of contamination of S2 by S3 is controlled by a purity, p, and thus S2=S1*p+S3*(1−p).

Simulated sequencing data is generated for each sample, using a Monte Carlo method to generate random samples of reads that conform to each site's genotype. This simulated data then provides a read count for each allele at each of the 10,000 sites under simulation, which can convected to an allele faction AF by dividing by the total read depth at each site.

Using the Variant Allele Fraction difference function:

$$d_{S1S2}(i) = \sum_{j=A,C,G,T} \text{abs}\left(AF_{S1}^i(i) - AF_{S2}^i(i)\right)$$

and using a weighting function that treats all sites equally (i.e. w(i)=1), we can calculate the difference score, $D_{S1,S2}$, using the equation above.

Calculating the difference woes between S1 and S2 as we vary the purity of sample S2 will enable us to estimate the effect that different levels of sample contamination has on the difference score from p=1.0 (no contamination) to p=0.0 (all contamination, effectively unrelated samples).

Figure 6:
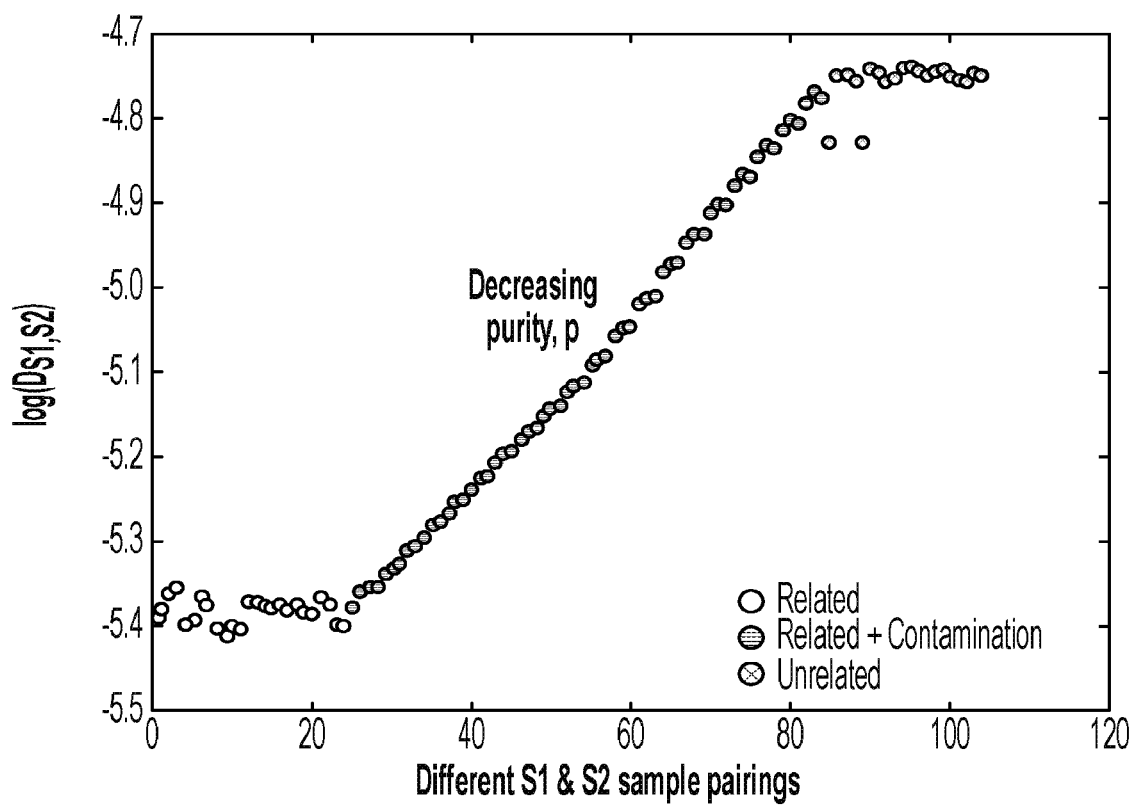
FIG. 6 depicts the result of a Monte Carlo simulation on sequencing data, illustrating the stability of the difference score with samples with no contamination.

FIG. 6 shows the result of just such a simulation. To show the stability of the difference score with samples with no contamination, we simulated 25 pairs of randomly generated samples S1 and S2, where p=1.0 (black dots). The next set of difference scores (blue dots) show the difference scones as purity of sample S2 decreases from p=1.0 to 0.0. The final set of dots show the difference scores of two completely unrelated samples, which are effectively identical to the scores received by contaminated samples where purity was 0.0.

This example can be extended by adjusting the weighting factor, w(i), such that only differences at only certain sites (e.g. sites representing exonic regions, or bases within genes of particular interest) are considered in the difference score (e.g. w(i)=0, for all elements i to be removed from difference calculation). This would have the effect of highlighting "contamination" or mutational drift at regions of the genome that must remain stable.

Example 3: Groupwise Difference Scores

The pairwise comparisons from above can be expanded to generate groupwise comparisons. For a group of n samples, the pairwise difference scores, $D_{ab}$, can be calculated for all unique sample pairings (where a=1, 2, . . . , n, b= 1, 2, . . . , n), generating a difference score matrix, D:

$$D = \begin{pmatrix} D_{11} & \cdots & D_{1n} \\ \vdots & \ddots & \vdots \\ D_{n1} & \cdots & D_{nn} \end{pmatrix}$$

which can be simplified to the following matrix, noting that the diagonal dements, $D_{ii}$, are zero and that elements $D_{ij}=D_{ji}$ according to the definitions of the above difference score calculations, which reduces the computational workload by N×N (N+:

$$D = \begin{pmatrix} 0 & \cdots & D_{1n} \\ \vdots & \ddots & \vdots \\ D_{n1} & \cdots & 0 \end{pmatrix}$$

With a matrix of difference scones generated for N samples, various numerical approaches (e.g. outlier analysis) and well-established clustering approaches (e.g. hierarchical clustering, k-means clustering, etc.) can be employed to analyze the samples (and their relationships) within the sample set.

Example 4: Outlier Analysis

Using a set of 4 highly related samples (e.g. clones with established genetic purity), we aim to test the purity of a $5^{th}$ sample (e.g. next generation of donor). We calculate the mean and standard deviation of pairwise difference scores amongst the set of 4 highly related samples, and determine if the $5^{th}$ sample falls within the expected bounds for all pairwise comparisons between it and the original 4 set of highly related samples:

PASS: $\max_{0<i<5} D_{i5} \leq \mu + c\sigma$

FAIL: $\max_{0<i<5} D_{i5} > \mu + c\sigma$ where $\mu$ is the mean of related samples, $\sigma$ is the standard deviation of related samples, and c is a factor that controls bow stringent the test (i.e. how many standard deviations from the mean are acceptable). The result of the above test could determine inclusion/exclusion from follow-on studies, deeper analytical investigations to determine the reason for any marked differences, etc.

Example 5: Cluster Analysis

Consider an experiment where 10 samples were produced (e.g. a series of cell line experiments grown under different selective environments) and the goal is to determine how many distinct populations are represented by the 10 samples, and then correlate the population structure with phenotypes (e.g. drug sensitivity, resistance).

The FIGS. 7 and 8 show the example dataset of 10 samples with pairwise difference scores measured as above. FIG. 7 shows the difference matrix, while FIG. 8 shows the sample data after clustering with an unsupervised clustering method. The clustering method identified 4 dusters (A, B, C, D) comprising 3, 4, 2, and 1 samples, respectively.

It should be apparent to those stilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one dement from the group, not A plus N, or B plus N, etc.

What is claimed is:

1. A computer-assisted method of determining genetic distances among a plurality of therapeutic cells, the method comprising:

obtaining omics data from a first genetic sequence string representing a first batch of therapeutic cells, a second genetic sequence string representing a second batch of therapeutic cells, and a reference sequence string, wherein the first and second genetic sequence strings represent the entire genome, transcriptome, or proteome of the first and second batch of therapeutic cells, wherein the first and second sequence strings have a plurality of corresponding sub-strings, and wherein the first and second sequence strings are stored in BAM or SAM file format;

providing access to an in-silico genetic database storing the first genetic sequence string the second genetic sequence string and the reference sequence string via at least one processor;

providing access to a sequence analysis engine coupled with the in-silico genetic database;

producing, using the sequence analysis engine and the at least one processor, a first local alignment by incrementally synchronizing the first and second sequence strings with the reference sequence string using a known position of at least one of plurality of corresponding substrings;

using, by the sequence analysis engine and the at least one processor, the first local alignment to generate a first local differential string set, wherein the first local differential string set identifies the differences between first sequence string and the reference sequence and the second sequence string and the reference sequence;

determining from the first local differential string set a first difference scone between the reference sequence and the first and second genetic sequence strings, wherein the first difference score is calculated by combining sub-scores, wherein a sub-score describes one or more attributes of the genetic sequence strings, wherein the first difference score $D_{ab}$ between a pair of samples a & b over n elements is formulated as a weighted average:

$$D_{ab} = \frac{\sum_{i=0}^{n} w(i)d_{ab}(i)}{\sum_{i=0}^{n} w(i)},$$

wherein w(i) is a per-element weighting factor and $d_{ab}(i)$ is a per-element difference score;

wherein w(i) is determined as follows:

(1) Exonic-Only Difference, where element i represents a position in the human genome:

$$w(i) = \begin{cases} 1 & \text{if } i = \text{exonic position} \\ 0 & \text{otherwise} \end{cases}$$

(2) Genes-of-Intent-Only Difference, where element i represents a human gene:

$$w(i) = \begin{cases} 1 & \text{if } i = \text{gene of interest} \\ 0 & \text{otherwise} \end{cases}$$

or (3) Disruptive Variants Difference, where element i represents a detected variant:

$$w(i) = \begin{cases} 1.0 & \text{if } i = \text{nonsense or frameshift indel} \\ 0.5 & \text{if } i = \text{missense or in-frame indel} \\ 0.0 & \text{otherwise} \end{cases}$$

wherein $d_{ab}(i)$ is determined as follows:

(i) Variant Allele Fraction, where element i represents a position in the human genome, and AF represents the allele fraction of each base (A, C, G, T) at that position:

$$d_{ab}(i) = \sum_{j=A,C,G,T} \text{abs}\left(AF_a^j(i) - AF_b^j(i)\right)$$

(ii) Gene expression differ where element i represents a gene, and EXP represents a measure of gene expression:

$$d_{ab}(i) = \text{abs}(EXP_a(i) - EXP_b(i))$$

or (iii) Microsatellite instability, where element i represents a single microsatellite locus, and MS represents a count of the different numbers of repeats at the locus, a measure of the site's instability:

$$d_{ab}(i)=\text{abs}(MS_a(i)-MS_b(i))$$

certifying the first and second batch of therapeutic cells as homogenous when the first difference score is under a predetermined threshold; and administering, upon determining homogeneity, the first or second batch of therapeutic cells to a patient in need thereof.

2. The method of claim 1, wherein the first and second genetic sequence strings represent at least 10% of a genome, transcriptome, or proteome of the first and biological samples, respectively.

3. The method of claim 1, wherein the first and second genetic sequence strings represent substantially the entire genome, transcriptome, or proteome of the first and second biological samples, respectively.

4. The method of claim 1, wherein the first and second biological samples originate from the same biological entity, the biological entity selected from the group consisting of a patient, a healthy individual, a cell line, a stem cell, an experimental animal model, a recombinant bacterial cell, and a virus.

5. The method of claim 1, wherein the corresponding substrings comprise homozygous alleles.

6. The method of claim 1, wherein the corresponding substrings comprise heterozygous alleles.

7. The method of claim 1, wherein the step of synchronizing comprises aligning at least one of the plurality of substrings is based on an a priori known location within the first string.

8. The method of claim 1, wherein the step of synchronizing comprises aligning at least one of the plurality of substrings based on a known reference string comprising known locations for the at least one of the plurality of substrings.

9. The method of claim 1, wherein the local differential string comprises a nucleic acid sequence that is different between the first and second genetic sequence strings.

10. The method of claim 9, wherein the difference score is associated with a length of the nucleic acid sequences.

11. The method of claim 9, wherein the difference score is associated with a number of nucleotides that are different between the first and second genetic sequence strings.

12. The method of claim 1, wherein the local differential string set comprises a plurality of local differential strings between the first and second sequence strings within the local alignment.

13. The method of claim 1, further comprising comparing the first difference scone with a threshold value to thereby determine the first genetic distance.

14. The method of claim 13, wherein the first genetic distance is calculated based on the difference between the threshold value and the first difference score.

15. The method of claim 1, wherein the genetic database stores a third genetic sequence string representing a third biological sample, and second and third local alignments are produced, using the sequence analysis engine, by incrementally synchronizing the first and third sequence strings and second and third sequence strings, respectively, using a known position of at least one of plurality of corresponding sub-strings.

16. The method of claim 15, further comprising:

using, by the sequence analysis engine, the second and third local alignments to generate a second and third local differential string sets between the first and third, and between the second and third sequence strings within the local alignment, respectively, wherein the second and third local differential string sets comprise at least one local different string;

determining from the second and third local differential string sets a second and third difference scores between the first and third, and second and third genetic sequence swings, respectively; and using the second and third difference scores to determine the second and third genetic distance between the first and third, and second and third biological samples, respectively.

17. The method of claim 16, further comprising comparing the second and third difference scores with a threshold value to thereby determine second and third genetic distances.

18. The method of claim 17, further comprising excluding the third biological sample from a group as an outlier sample if the second and third genetic distances are at least 50% farther than the first genetic distance.

* * * * *